(12) United States Patent
Kuroki et al.

(10) Patent No.: US 6,746,586 B2
(45) Date of Patent: Jun. 8, 2004

(54) MULTI-LAYER GAS SENSOR ELEMENT AND GAS SENSOR COMPRISING THE SAME

(75) Inventors: Yoshiaki Kuroki, Aichi (JP); Kunio Yanagi, Aichi (JP); Tomohiro Mabuchi, Aichi (JP); Shinya Awano, Aichi (JP); Hiroyuki Hayashi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/917,874

(22) Filed: Jul. 31, 2001

(65) Prior Publication Data

US 2002/0036138 A1 Mar. 28, 2002

(30) Foreign Application Priority Data

Jul. 31, 2000 (JP) .......................... 2000-232400

(51) Int. Cl.$^7$ ............................................. G01N 27/407
(52) U.S. Cl. ........................................ 204/429; 204/424
(58) Field of Search ................................ 204/429, 424, 204/426, 428; 73/23.32

(56) References Cited

U.S. PATENT DOCUMENTS

| 4,221,650 A | * | 9/1980 | Friese et al. ................ 204/429 |
| 4,595,485 A | | 6/1986 | Takahashi et al. |
| 4,642,174 A | * | 2/1987 | Shibata ....................... 204/408 |
| 4,661,234 A | | 4/1987 | Takahashi et al. |
| 4,798,693 A | | 1/1989 | Mase et al. |
| 5,522,979 A | | 6/1996 | Tatumoto ..................... 204/429 |

FOREIGN PATENT DOCUMENTS

| EP | 0059933 | 9/1982 |
| EP | 0059933 | 8/1985 |
| EP | 0686847 A2 | 12/1995 |

OTHER PUBLICATIONS

Practical Handbook of Materials Sciene, Charles Lynch (ed.), pp. 299,310,and 311, 1989.*

* cited by examiner

Primary Examiner—Kaj K. Olsen
(74) Attorney, Agent, or Firm—Sughrue Mion, PLLC

(57) ABSTRACT

A multi-layer gas sensor element is described which comprises a solid electrolytic member, a substrate, and a porous member, wherein each of the substrate and the porous member has a thickness larger than that of the solid electrolytic member with respect to a lamination direction; the substrate and the porous member face each other and sandwich the solid electrolytic member; a ceramic component constituting the substrate in the highest volume percent is the same as the ceramic component constituting the porous member in the highest volume percent thereof; and the volume percent (R2) of the ceramic component contained in the porous member is 80% or more the volume percent (R1) of the ceramic component contained in the substrate.

17 Claims, 3 Drawing Sheets

LONGITUDINAL DIRECTION

WIDTH DIRECTION

WARPAGE +

WARPAGE −

MULTI-LAYER GAS SENSOR ELEMENT AND GAS SENSOR COMPRISING THE SAME

FIELD OF THE INVENTION

The present invention relates to a multi-layer gas sensor element and a gas sensor including the element. More particularly, the present invention relates to a multi-layer gas sensor element including a porous body, which element produces minimal warpage and does not suffer exfoliation, cracking, etc.; i.e., which element exhibits high durability; and a gas sensor including the gas sensor element, which sensor is highly resistant to poisoning by exhaust gas.

BACKGROUND OF THE INVENTION

Conventional multi-layer gas sensor elements (hereinafter referred to simply as "elements") have been employed in a gas sensor (such as an oxygen sensor, an HC sensor, or an $NO_x$ sensor) for detecting a specific component contained in exhaust gas of, for example, an internal combustion engine, and measuring the concentration of the component. In some cases, such a gas sensor element includes a porous body for covering a detection electrode which is brought into contact with a gas to be detected, in order to protect the detection electrode from poisoning. However, warpage of conventional multi-layer gas sensor elements including a porous body has not heretofore been satisfactorily prevented. Therefore, conventional gas sensor elements have tended to suffer cracking due to such warpage.

SUMMARY OF THE INVENTION

The present invention contemplates solving the above-mentioned problems, and an object of the present invention is to provide a multi-layer gas sensor element including a porous body, which element produces minimal warpage and does not suffer exfoliation, cracking, etc.; i.e., which element exhibits high durability; and a gas sensor including the gas sensor element, which sensor exhibits high durability. $Al_2O_3$ can be used as the ceramic component for realization of.

Accordingly, the present invention provides a multi-layer gas sensor element comprising a solid electrolytic member, a substrate, and a porous member, wherein each of the substrate and the porous member has a thickness greater than that of the solid electrolytic member with respect to a lamination direction; the substrate and the porous member face each other and sandwich the solid electrolytic member; a ceramic component constituting the substrate in the highest volume percent thereof is the same as the ceramic component constituting the porous member in the highest volume percent thereof; and the volume percent (R2) of the ceramic component contained in the porous member is 80% or more the volume percent (R1) of the ceramic component contained in the substrate. Characteristic features of the multi-layer gas sensor element reside in minimization of the differences in shrinkage percentage between the substrate and the porous member during firing and the difference in thermal expansion therebetween during use.

As another aspect of the invention, in the gas sensor element of the present invention, when the mean grain size of crystals constituting the substrate is referred to as "a1" and the mean grain size of crystals constituting the porous member is referred to as "a2," the value A represented by the equation $$A = a1/a2 \quad (1)$$

preferably falls within a range between 0.9 and 5 inclusive, more preferably $1.0 \leq A \leq 3.25$, most preferably $1.0 \leq A \leq 2.0$. When the value A falls outside a range between 0.9 and 5 inclusive, warpage of the gas sensor element may fail to be satisfactorily prevented.

DESCRIPTION OF REFERENCE NUMERALS

Figure 1:
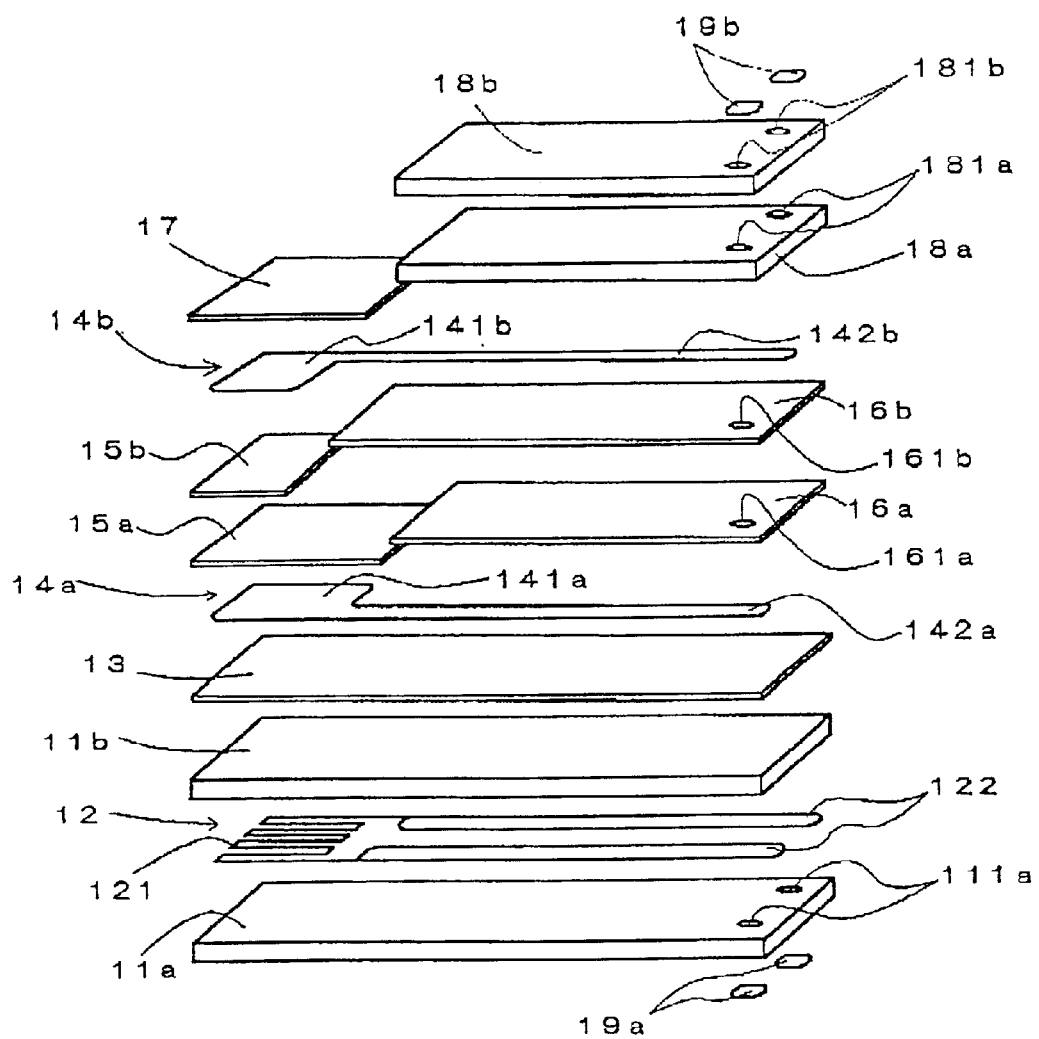
FIG. 1 is an exploded perspective view of an element according to the present invention.

1: gas sensor element
11a: first substrate
11b: second substrate
111a: through-hole
12: heating resistor
121: heating portion
122: heater lead portion
13: buffer layer
14a: reference electrode
14b: detection electrode
141a: reference electrode portion
142a: reference electrode lead portion
15a: first solid electrolytic member
15b: second solid electrolytic member
16a: first insulating layer
16b: second insulating layer
161a, 161b: through-hole
17: porous member
18a: first reinforcing layer
181a and 118b: through-holes
18b: second reinforcing layer
2: gas sensor
21: metallic shell
211: metallic shell screw portion

DETAILED DESCRIPTION OF THE INVENTION

The aforementioned "solid electrolytic member" may be a plate (generally having a thickness of 50 μm or more) or a thin film (generally having a thickness of less than 50 μm). The shape of the surface of the member is not particularly limited. The composition of the member is not particularly limited, so long as the member allows passage of oxygen ions therethrough. The member may be formed from, for example, a zirconia ($ZrO_2$)-containing sintered compact, an $LaGaO_3$-containing sintered compact, or such a sintered compact containing hafnium. The solid electrolytic member preferably contains the same component ($Al_2O_3$) that is predominantly contained in the substrate which is brought into direct or indirect contact with the solid electrolytic member, in an amount of 20–70 mass %, more preferably 30–50 mass %, on the basis of the entirety (i.e., 100 mass %) of the solid electrolytic member. When the amount of the component falls within the above range, in the resultant gas sensor element, adhesion between the solid electrolytic member and the layer is enhanced.

A reference electrode and a detection electrode are provided on the solid electrolytic member. The reference electrode is an electrode which is brought into contact with a reference gas, an electrode which is placed in an oxygen atmosphere of consistent pressure produced by means of the action of an oxygen pump, or an electrode which exhibits an electric potential higher than that of the detection electrode when being brought into contact with a combustible gas component contained in a gas to be detected. The detection electrode is an electrode which is brought into contact with a gas to be detected. The reference electrode and the detection electrode may be formed on the same surface or on different surfaces of the solid electrolytic member. No particular limitation is imposed on the component constituting each of the reference electrode and the detection electrode. Each electrode predominantly contains Pt and may contain Au, Ag, Pd, Ir, Ru, or Ph. Pt is preferred, since it effectively mediates the reaction between the solid electrolytic member and oxygen. The compositions of the reference electrode and the detection electrode may be identical to or different from each other.

The aforementioned "substrate" may be formed directly on the solid electrolytic member. Alternatively, the substrate may be formed such that the substrate and the solid electrolytic member sandwich a layer having a different function (e.g., a buffer layer which is provided between a solid electrolytic member and a substrate including a heating resistor and suppresses thermal expansion, or a reference electrode). Furthermore, the substrate may include a heating resistor which can produce heat by means of power supplied from the outside to thereby activate the solid electrolytic member.

The relative density of the substrate is preferably 97% or more, more preferably 98% or more, much more preferably 98–100%. When the relative density of the substrate is less than 95%, the resultant gas sensor element may fail to have satisfactory mechanical strength. The term "relative density" refers to the percentage D (%) calculated by the following formula (2), when the theoretical density of the substrate calculated on the basis of the composition of the substrate, which composition is obtained in advance through ultimate analysis, is referred to as "$\rho 1$," and the actual density of the substrate measured by means of Archimedes' principle is referred to as "$\rho 2$."

$$D(\%)=\{\rho 2/\rho 1\}\times 100 \quad (2)$$

The aforementioned "porous member" is usually formed so as to be brought into contact directly with the solid electrolytic member and the detection electrode. The porous member is a layer having the following functions (1) through (3): (1) a function for protecting the detection electrode, which is brought into contact with a gas to be detected, from poisoning by, for example, Si, P, Pb, or a compound containing such an element; (2) a function for preventing cracking of the multi-layer gas sensor element during use, the cracking otherwise being caused by adhesion of water droplets; and (3) a function for equilibrating gas components constituting a gas to be detected by allowing the gas to pass through the porous member.

In another aspect of the invention, the relative density of the porous member is preferably 40–85%, and more preferably 50–75%. When the relative density of the porous member is less than 40%, the porous member may fail to satisfactorily exert the effect of protecting the detection electrode from poisoning, particularly, from poisoning by microparticles of silicon oxide. In contrast, when the relative density of the porous member is in excess of 85%, a certain time elapses before a gas to be detected reaches the surface of the detection electrode, and thus accurate detection may fail to be carried out. Particularly, the porous member may fail to satisfactorily exert the effect of protecting the detection electrode from poisoning by a substance contained in exhaust gas and having a relatively large particle size, such as lead or P, since pores of the porous member become stuffed with such a substance.

In a further aspect of the invention, the porosity of the porous member is preferably 15–60%, and more preferably 25–50%. When the porosity is less than 15%, a certain time elapses before a gas to be detected reaches the surface of the detection electrode, and thus accurate detection and control of exhaust gas may fail to be carried out. Particularly, the porous member may fail to satisfactorily exert the effect of protecting the detection electrode from poisoning by a substance contained in exhaust gas and having a relatively large particle size, such as lead. In contrast, when the porosity is in excess of 65%, the porous member may fail to satisfactorily exert the effect of protecting the detection electrode from poisoning, particularly, from poisoning by microparticles of silicon oxide. The term "porosity" refers to the percentage P calculated by the following formula (3) by use of the apparent volume (V) of the porous member (including the volume of pores), the mass of the member in air (m1), the mass of the member when being immersed in water (m2), and the mass of the member in the case in which the member is immersed in water and then water is sufficiently incorporated into pores of the member by means of a degassing technique such as vacuum degassing or degassing through boiling (m3).

$$P(\%)=\{(m3-m1)/(m3-m2)\}\times 100 \quad (3)$$

Each of the substrate and the porous member has a thickness greater than that of the solid electrolytic member with respect to a layer-stacking direction. Therefore, warpage of the gas sensor element can be effectively prevented. The average thickness of each of the substrate and the porous member is preferably more than that of the solid electrolytic member. Especially it is preferably at least 1.5–2.0 times that of the solid electrolytic member. When the average thickness of each of the substrate and the porous member is less than 1.5 times that of the solid electrolytic member, the gas sensor element is inclined to produce warpage easily. When the average thickness of the porous member is excessively large, the resultant gas sensor may encounter difficulty in carrying out accurate detection. The term "average thickness" refers to the average of thicknesses in a layer-stacking direction, which are measured at five or more different points. The thicknesses of the substrate and the porous member may be identical to or different from each other.

The aforementioned phrase "the substrate and the porous member face each other" refers to the situation in which the substrate and the porous member face each other with respect to a layer-stacking direction. The substrate and the porous member do not necessarily have the same shape. Furthermore, the substrate and the porous member do not necessarily have the same length and do not necessarily face each other over their entire areas.

No particular limitation is imposed on the component constituting each of the substrate and the porous member, but a ceramic component (e.g., an oxide such as $Al_2O_3$ or $ZrO_2$) constituting the substrate in the highest volume percent thereof is the same as the ceramic component constituting the porous member in the highest volume percent thereof. Preferably, a ceramic component constituting the substrate in the second highest volume percent thereof is the same as the ceramic component constituting the porous member in the second highest volume percent thereof.

The volume percent (R2) of a ceramic component of highest volume percent contained in the porous member is 80% or more the volume percent (R1) of the ceramic component contained in the substrate. Preferably, the volume percent (R2) is 90% or more the volume percent (R1). More preferably, the volume percent (R2) is 95% or more the volume percent (R1). When the volume percent (R2) is less than 80% the volume percent (R1), warpage of the gas sensor element may fail to be satisfactorily prevented. The amount of the ceramic component contained in the substrate is preferably 80 vol % or more, more preferably 90 vol % or more, and much more preferably 95 vol % or more.

The volume percent of the ceramic component can be measured by subjecting the cross section of the substrate to mirror polishing, and by analyzing the cross section through X-ray photoelectron spectroscopy (XPS).

The volume percent (R2') of crystals formed of a ceramic component of highest volume percent contained in the porous member is preferably 60% or more the volume percent (R1') of crystals formed of the ceramic component contained in the substrate. More preferably, the volume percent (R2') is 70% or more the volume percent (R1'). Much more preferably, the volume percent (R2') is 80% or more the volume percent (R1').

As described above, the ceramic component constituting the substrate is not particularly limited, but preferably, the substrate predominantly contains alumina and/or zirconia, or the substrate contains alumina or zirconia. Particularly, the substrate preferably contains at least alumina. The amount of alumina contained in the substrate is preferably 70 vol % or more, more preferably 80 vol % or more, on the basis of the entirety (i.e., 100 vol %) of the substrate. Furthermore, the substrate preferably has an insulating value 100 times or more that of the solid electrolytic member at 900° C.

The mean grain size a1 or a2 is obtained as follows. The cross section of each of the substrate and the porous member is subjected to mirror polishing; an electron micrograph of the cross section is obtained; a rectangle is inscribed in each crystal in the obtained electron micrograph of the cross section; the average of the sum of the length and the width of the rectangle is regarded as the grain size of each crystal; and the average of the grain sizes of all the crystals in the electron micrograph (actual size: 30 μm square) is calculated.

When the multi-layer gas sensor element has the structure as described in the present invention, the element produces minimal warpage. Therefore, occurrence of cracking, which is attributed to warpage of the element, can be prevented to a great extent.

The term "warpage" as used herein will be described below. As shown in FIGS. 3(a) and 3(b), when the height of a cuboid in which the gas sensor element is inscribed is referred to as "d1," the height of the element having a relatively small strain with respect to a width direction is referred to as "d2," and "d1–d2" is 200 μm or more, the element is considered to warp (note: the length of the cuboid (d3) is usually 37.5 mm). When "d1–d2" is in excess of 600 μm, the element may be prone to cracking when fired or during use. Notably, the warpage as measured in the above-described manner is an index that represents an amount of warpage as measured over the entire length of the element, including not only the vicinity of the detection portion but also other portions; however, in the present specification, the warpage as measured in the above-described manner is used as an index representing warpage at the detection portion.

The gas sensor of the invention includes the multi-layer gas sensor element as described in the various embodiments described above.

The structure of a gas sensor 2 is not particularly limited. For example, a gas sensor element 1 is provided in a metallic shell 21, and the sensor is screwed into, for example, an exhaust pipe by means of a metallic shell screw portion 211 formed outside the shell 21 such that a detection portion of the element provided at the front-side portion of the sensor projects into the exhaust pipe, and is exposed to a gas to be detected (see FIG. 2).

The gas sensor exhibits high durability, since the sensor barely involves problems attributed to cracking of the gas sensor element.

EXAMPLES

Figure 2:
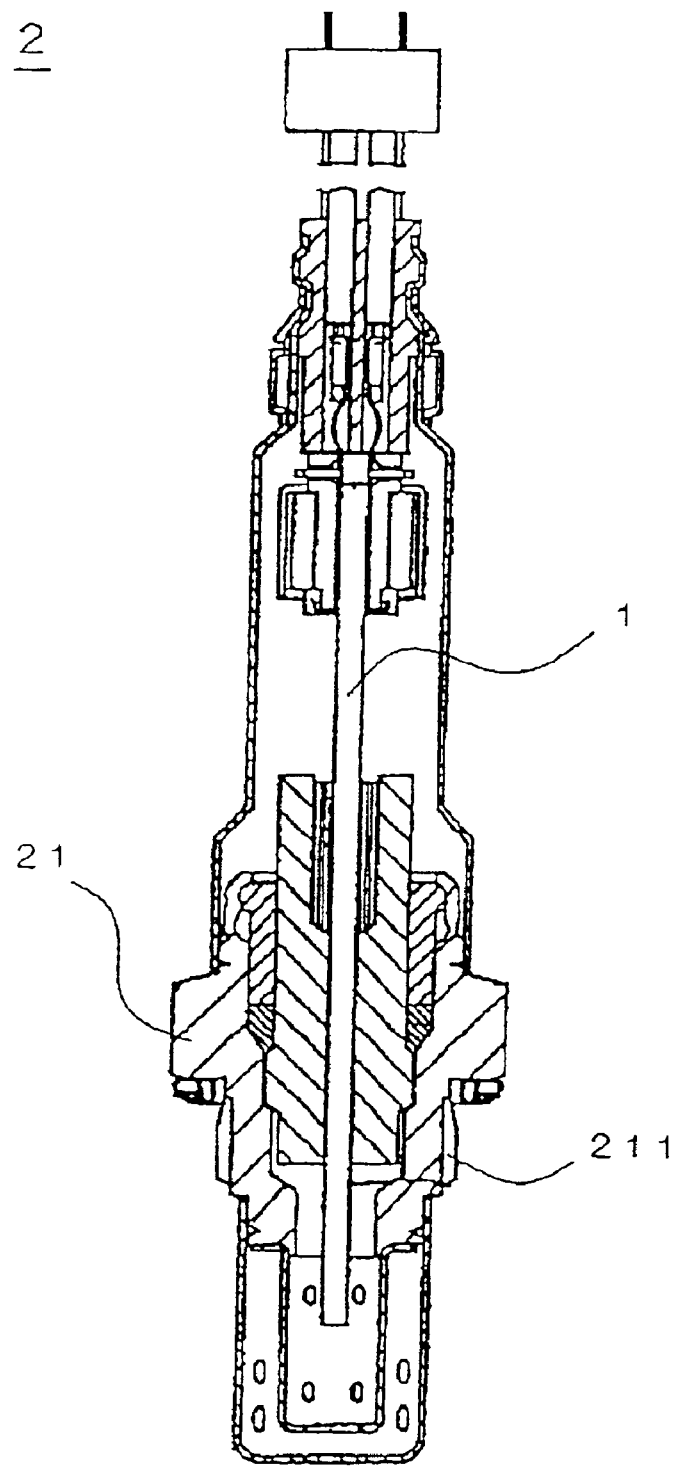
FIG. 2 is a cross-sectional view of a gas sensor according to the present invention.
Figure 3:
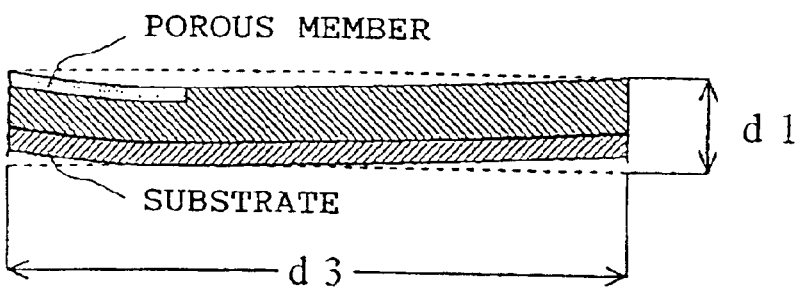
FIG. 3(a) is a schematic representation for explaining d1.
FIG. 3(b) is a schematic representation for explaining d2.
FIG. 3(c) and FIG. 3(d) are schematic representations for explaining warpage of an element.
Figure 3:
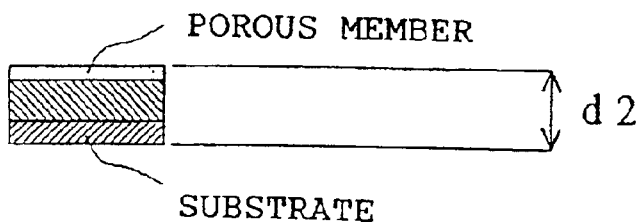
Figure 3:
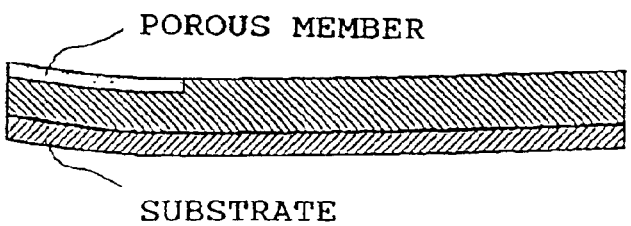
Figure 3:
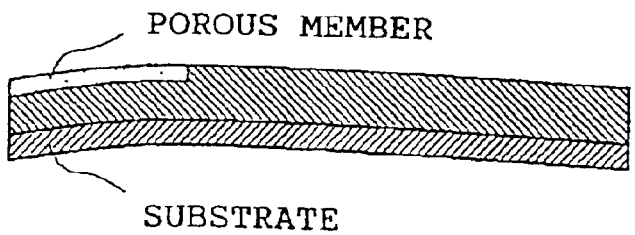

With reference to FIGS. 1, 2 and 3, the present invention will next be described in more detail by way of examples.
1. Production of Element In order to simplify the description, the production process will be described by taking, as an example, production of an element in which patterns are printed on a sheet having a size of one element, and layers are laminated. However, in practice, patterns were formed through printing on a green sheet having a large size such that a plurality of elements can be produced; layers were laminated; the resultant multi-layer product was cut into green products having an element shape; and each green product was subjected to degreasing and firing, to thereby produce an element.
(1) Preparation of Green Sheet for Substrate Alumina powder (purity: 99.99% or more, mean particle size: 0.3 μm) (100 parts by mass (hereinafter simply referred to as "parts")) was mixed with a butyral resin (14 parts) and dibutyl phthalate (7 parts). The resultant mixture was mixed with a solvent mixture of toluene and methyl ethyl ketone, to thereby prepare a slurry. A green sheet for a first substrate and a green sheet for a second substrate were formed from the slurry through a doctor blade process. Subsequently, through holes 111a were formed at predetermined positions of the green sheet for a first substrate. The green sheet for a first substrate has a thickness of 0.45 mm, a length of 5 cm, and a width of 4.5 mm. After being fired, the green sheet becomes a first substrate 11a. The green sheet for a second substrate has a thickness of 0.25 mm, a length of 5 cm, and a width of 4.5 mm. After being fired, the green sheet becomes a second substrate 11b.
(2) Formation of Heater Pattern Alumina powder (purity: 99.99% or more, mean particle size: 0.3 μm) (4 parts) was mixed with platinum powder (100 parts). To the resultant mixture were added a binder (6 parts) and dibutyl phthalate (25 parts), to thereby prepare a paste for a conductive layer. Through printing, the paste was applied in a heating portion pattern (i.e., a heating portion 121 after firing) onto a first surface of the green sheet for a first substrate (i.e., a first substrate 11a after firing) and dried. Subsequently, through printing, the paste was applied in a heater lead pattern (i.e., a heater lead portion 122 after firing) onto the first surface of the green sheet and dried, to thereby form a heater pattern (i.e., heating resistor 12 after firing). Subsequently, through printing, the paste was applied in heating resistor terminal patterns (i.e., heating resistor terminals 19a after firing) in the vicinity of the end of a second surface of the green sheet for a first substrate, such that the heating resistor 12 conducted to the terminals 19a through the through holes 111a, and the paste was dried. Thereafter, the green sheet for a second substrate (i.e., the upper half of the substrate after firing) was formed on the heater pattern, and connected to the green sheet for a first substrate through pressing.

(3) Formation of Buffer Layer Pattern

Alumina (80 parts) was mixed with a zirconia (20 parts), to thereby prepare a paste for a buffer layer. Through printing, the paste was applied in a buffer layer pattern (i.e., a buffer layer 13 after firing) (thickness: 40±10 μm) onto the green sheet for a second substrate of the ceramic multi-layer product formed in step (2), and the paste was dried.

(4) Formation of Reference Electrode Pattern

A paste for electrode formation was prepared in the same manner as that used for preparing the paste for a conductive layer used in the step (2), except that powder of partially-stabilized zirconia (20 parts) (purity: 99.9% or more, mean particle size: 0.3 μm) was used in place of alumina powder. Through printing, the paste for electrode formation was applied in a reference electrode pattern (i.e., a reference electrode 14a after firing) (thickness: 20±10 μm) including a reference electrode portion pattern (i.e., a reference electrode portion 141a after firing) and a reference electrode lead portion pattern (i.e., a reference electrode lead portion 142a after firing) onto the buffer layer pattern formed in step (3), and the paste was dried.

(5) Formation of First Solid Electrolytic Member Pattern

To zirconia powder (purity: 99.9% or more, mean particle size: 0.3 μm) (50 parts) were added alumina powder (purity: 99.99% or more, mean particle size: 0.3 mm) (50 parts), butylcarbitol (33.3 parts), dibutyl phthalate (0.8 parts), a dispersant (0.5 parts), a binder (20 parts), and acetone (a predetermined amount), and the resultant mixture was mixed for four hours. Subsequently, acetone was evaporated, to thereby prepare a paste for a solid electrolytic member.

The paste for a solid electrolytic member was applied through printing so as to cover the reference electrode pattern and dried, to thereby form a first solid electrolytic member pattern (i.e., a first solid electrolytic member 15a after firing) having a length of 13 mm and a thickness of 25±10 μm.

(6) Formation of First Insulating Layer Pattern

Butylcarbitol (50 parts) and acetone (a predetermined amount) were added to the slurry for a green sheet prepared in step (1), and the resultant mixture was mixed for four hours. Subsequently, acetone was evaporated, to thereby prepare a paste for an insulating layer. Through printing, the paste for an insulating layer was applied onto a portion of the buffer layer pattern on which the first solid electrolytic pattern had not been printed, and dried, to thereby form a first insulating layer pattern (i.e., a first insulating layer 16a after firing) having a thickness of 25±10 μm. The paste was not applied onto a portion corresponding to a through-hole 161a.

(7) Formation of Second Solid Electrolytic Member Pattern

Through printing, the paste for a solid electrolytic member prepared in the step (5) was applied onto the first solid electrolytic member so as to form a second solid electrolytic member pattern (i.e., a second solid electrolytic member 15b after firing), which extends from the tip end portion and has a length of 6.5 mm and a thickness of 25±10 μm.

(8) Formation of Second Insulating Layer Pattern

Through printing, the paste for an insulating layer prepared in the step (6) was applied onto the first solid electrolytic pattern and the first insulting layer pattern so as to cover a portion on which the second solid electrolytic pattern had not been printed, and dried, to thereby form a second insulating layer pattern (i.e., a second insulating layer 16b after firing) having a thickness of 25±10 μm. The paste was not applied onto a portion corresponding to the through-hole 161b.

(9) Formation of Detection Electrode Pattern

Through printing, the paste for a conductive layer prepared in the step (4) was applied onto the second solid electrolytic member pattern formed in step (7) and the second insulating layer pattern formed in step (8) in a detection electrode pattern (i.e., a detection electrode 14b after firing) (thickness: 20±10 μm) including a detection electrode portion pattern (i.e., a detection electrode portion 141b after firing) and a detection electrode lead portion pattern (i.e., a detection electrode lead portion 142b after firing), and the paste was dried.

(10) Preparation and Lamination of Green Sheet for Reinforcing Layer

The raw materials employed in step (1) were mixed in the same compositional proportions as those described in step (1), to thereby prepare a slurry. A green sheet for a first reinforcing layer and a green sheet for a second reinforcing layer were formed from the slurry through a doctor blade process. The green sheet for a first reinforcing layer has a thickness of 0.25 mm and a length of 3.5 cm. After being fired, the green sheet becomes a first reinforcing layer 18a. Through-holes 181a are formed at the end portion of the green sheet. The green sheet for a second reinforcing layer has a thickness of 0.4 mm and a length of 3.5 cm. After being fired, the green sheet becomes a second reinforcing layer 18b. Through-holes 18b are formed at the end portion of the green sheet.

Subsequently, the green sheet for a first reinforcing layer was laminated so as to cover the detection electrode lead portion pattern of the detection electrode pattern formed in step (9). Thereafter, the green sheet for a second reinforcing layer was laminated onto the green sheet for a first reinforcing layer.

(11) Formation of Electrode Terminal Pattern

Through printing, the conductive paste prepared in step (4) was applied in electrode terminal patterns (i.e., electrode terminals 19b after firing) onto positions corresponding to the through-holes 181b, and dried. The electrode terminals are employed for inputting or outputting electric signals to or from each of the reference electrode and the detection electrode.

(12) Preparation and Lamination of Green Sheet for Porous Member

In a manner similar to that of step (1), alumina powder (purity: 99.99% or more, mean particle size: 0.3 μm) (100 parts) was mixed with carbon powder (spherical powder, mean particle size: 7.5 μm) (30 parts), a butyral resin (12 parts), and dibutyl phthalate (6 parts). The resultant mixture was mixed with a solvent mixture of toluene and methyl ethyl ketone, to thereby prepare a slurry. Through a doctor blade process, the slurry was shaped into a sheet having a thickness of 450 μm. Subsequently, the resultant sheet was cut into pieces having a length of 10 mm and a width of 4.5 mm, to thereby prepare green sheets for a porous member.

The resultant green sheet for a porous member (i.e., a porous member 17 after firing) was laminated so as to cover the detection electrode portion pattern formed in step (9).

In order to prepare the green sheet for a porous member, a paste for the green sheet was prepared such that, when the mass of a binder for the substrate on the basis of unit surface area of ceramic raw material powder (alumina) for the substrate is referred to as "B1" ($g/m^2$), and the mass of a binder for the porous member (butyral resin) on the basis of unit surface area of ceramic raw material powder for the porous member is referred to as "B2" ($g/m^2$), the value X represented by the following formula (4) falls within a range between −0.1 and 0.1.

$$X = (B1 - B2)/B1 \qquad (4)$$

When the paste is prepared as described above, the amount of the binder on the basis of unit surface area of ceramic raw material powder for the green sheets for first and second substrates is substantially equal to that of the binder on the basis of unit surface area of ceramic raw material powder for the green sheet for the porous member. Therefore, the difference in shrinkage percentage between the green sheet for the substrate and the green sheet for the porous member can be maintained within 7% during firing at a temperature of 1,200–1,500° C.

(13) Degreasing and Firing

The temperature of the multi-layer product formed in steps (1) through (12) was elevated in air from room temperature to 420° C. at a rate of 10° C./hour. Subsequently, the temperature of the product was maintained at 420° C. for two hours, to thereby remove the organic binder from the product. Thereafter, the temperature of the product was elevated in air to 1,100° C. at a rate of 100° C./hour, and then elevated to 1,520° C. at a rate of 60° C./hour. The temperature of the product was maintained at 1,520° C. for one hour for firing the product, to thereby produce an element 1.

2. Production of Element in Which Properties of Substrate and Porous Member are Changed The percentage of alumina powder or zirconia powder which was incorporated into the green sheet in steps (1) and (12) of the steps (1) through (12) in [1] and the particle size of the powder were changed, to thereby produce elements in which the volume percent of a ceramic component of highest volume percent contained in the substrate or the porous member and the mean grain size of crystals differed (300 elements for each of Test Examples 1 through 24). In each Test Example, five elements were randomly selected from the 300 elements, R1, R2, and R2/R1 in relation to each of the five elements were calculated, and the average values of R1, R2, and R2/R 1 were obtained. The results are shown in Tables 1 and 2. Furthermore, in each Test Example, one element was randomly selected from the 300 elements, and a micrograph of the element was obtained by use of an electron microscope. By use of the micrograph, a1, a2, and a1/a2 in relation to the element were calculated. The results are shown in Tables 1 and 2.

3. Measurement of Warpage and Evaluation of Exfoliation and Cracking

Five elements were randomly selected from the elements produced through the procedures (1) and (2), and the degree of warpage of the five elements was measured by calculating the average of "d1–d2" {see FIGS. 3(a) and 3(b)} of the

TABLE 1

| Test Ex. | Predominant component of substrate and porous member | Volume percent (vol %) | | | Mean particle size (μm) | | | Warpage after firing (μm) | Exfoliation and cracking after firing | Cracking after cooling-heating cycle test |
|---|---|---|---|---|---|---|---|---|---|---|
| | | R1 (in substrate) | R2 (in porous member) | R2/R1 | a1 (substrate) | a2 (porous member) | A (a1/a2) | | | |
| 1 | Alumina | 99.99 | 99.99 | 100 | 2.3 | 2.6 | **0.88 | 0.8 | 0/300 | 53/300 |
| 2 | | 99.99 | 99.99 | 100 | 2.3 | 2.3 | 1.00 | 0.05 | 0/300 | 0/300 |
| 3 | | 99.99 | 99.99 | 100 | 2.3 | 1.2 | 1.92 | 0.1 | 0/300 | 0/300 |
| 4 | | 99.99 | 99.99 | 100 | 3.9 | 1.2 | 3.25 | 0.4 | 0/300 | 0/300 |
| 5 | | 99.99 | 99.99 | 100 | 4.1 | 0.8 | **5.13 | 0.7 | 0/300 | 0/300 |
| 6 | | 99.99 | 99.99 | 100 | 4.3 | 0.7 | **6.14 | 1 | 0/300 | 22/300 |
| 7 | | 99.99 | 80 | 80 | 4.0 | 4.0 | 1.00 | −0.3 | 0/300 | 0/300 |
| *8 | | 99.99 | 75 | *75 | 3.9 | 3.8 | 1.03 | −0.4 | 9/300 | 30/291 |
| *9 | | 99.99 | 70 | *70 | 4.1 | 3.9 | 1.05 | −0.6 | 34/300 | 107/266 |
| 10 | | 90 | 90 | 100 | 4.2 | 3.9 | 1.08 | 0.1 | 0/300 | 0/300 |
| 11 | | 80 | 80 | 100 | 3.8 | 4.1 | 0.93 | 0.1 | 0/300 | 0/300 |
| 12 | | 70 | 70 | 100 | 3.9 | 4.0 | 0.98 | 0.05 | 0/300 | 0/300 |

Values marked with * fall outside of the required range of R2/R1, and values marked with ** fall outside of the optimal range of A.

TABLE 2

| Test Ex. | Predominant component of substrate and porous member | Volume percent (vol %) | | | Mean particle size (μm) | | | Warpage after firing (μm) | Exfoliation and cracking after firing | Cracking after cooling-heating cycle test |
|---|---|---|---|---|---|---|---|---|---|---|
| | | R1 (in substrate) | R2 (in porous member) | R2/R1 | a1 (substrate) | a2 (porous member) | A (a1/a2) | | | |
| 13 | Alumina | 60 | 60 | 100 | 4.1 | 3.8 | 1.08 | 0.2 | 0/300 | 0/300 |
| 14 | | 80 | 80 | 100 | 4.2 | 2.3 | 1.83 | −0.1 | 0/300 | 0/300 |
| 15 | | 80 | 70 | 88 | 3.9 | 1.2 | 3.25 | −0.2 | 0/300 | 0/300 |
| 16 | | 80 | 65 | 81 | 4.0 | 0.8 | 5.00 | −0.3 | 0/300 | 0/300 |
| *17 | | 80 | 60 | *75 | 4.1 | 0.8 | **5.13 | −0.5 | 8/300 | 4/292 |
| *18 | | 80 | 50 | *63 | 4.2 | 0.8 | **5.25 | −1.1 | 52/300 | 241/248 |
| 19 | Zirconia | 95 | 95 | 100 | 2.1 | 2.0 | 1.05 | 0.05 | 0/300 | 0/300 |
| 20 | | 95 | 90 | 95 | 2.4 | 1.4 | 1.71 | −0.1 | 0/300 | 0/300 |
| 21 | | 95 | 80 | 84 | 1.8 | 1.6 | 1.13 | −0.2 | 0/300 | 0/300 |
| *22 | | 95 | 70 | *74 | 2.4 | 2.0 | 1.20 | −0.4 | 5/300 | 21/295 |
| *23 | | 95 | 60 | *63 | 2.0 | 2.1 | 0.95 | −1 | 17/300 | 47/283 |
| *24 | | 95 | 50 | *53 | 1.8 | 1.9 | 0.95 | −2 | 49/300 | 126/251 |

Values marked with * fall outside of the required range of R2/R1, and values marked with ** fall outside of the optimal range of A.

elements immediately after firing. The results are shown in Tables 1 and 2. Furthermore, each of the five elements was placed such that the porous member was on the upper side. When the element was curled upward, "+" was assigned to the value "d1–d2," and when the element was curled downward, "–" was assigned to the value "d1–d2" {see FIGS. 3(c) and 3(d)}. The results are shown in Tables 1 and 2.

In addition, all the 300 elements of each of Test Examples 1 through 24 were subjected to vacuum immersion in water-soluble red ink for 10 minutes, and then washed with water. Thereafter, exfoliation and cracking of each element were observed. The results are shown in Tables 1 and 2.

4. Cooling-Heating Cycle Durability Test

All the elements of each of Test Examples 1 through 24 produced through the procedure (1) and (2), except the elements which suffered exfoliation and cracking after firing, were subjected to the following heating cycle test: a voltage of 16 V was applied to the heating resistor of each element, to thereby heat the element until the temperature of the solid electrolytic member reached about 1,000° C.; and subsequently, application of the voltage was stopped, and the element was allowed to stand until the temperature of the solid electrolytic member was lowered to room temperature. The heating cycle test was repeated 10 times for each element. Thereafter, exfoliation and cracking of each element were observed in a manner similar to that of (3). The results are shown in Tables 1 and 2.

5. Evaluation of Resistance to Poisoning on the Basis of Relative Density and Porosity of Porous Member In each of Test Examples 25 through 31, the procedure of (1) was repeated, except that the amount of carbon powder was changed in step (12), to thereby produce an element including a porous member having a relative density and a porosity shown in Table 3.

Subsequently, an oxygen sensor including the resultant element was provided in the discharge system of a heated engine of 1,800 cc, and the response speed of the sensor was evaluated when the ratio of fuel to air was changed every three seconds so as to attain rich and lean states. The engine was operated by use of gasoline containing lead (Pb) in an amount of 50 mg per gallon of gasoline, and gasoline. The response speed of the oxygen sensor was evaluated after 500 hours of the engine exhaust gas exposure cycles of 450° C. (1 hour)–850° C. (3 hours). The results are shown in Table 3.

Furthermore, the engine was operated by use of gasoline containing 0.12 cc silicon (Si) per liter of gasoline. The response speed of the oxygen sensor was evaluated after 18 hours of the engine exhaust gas exposure of 400° C. The test result are shown table 3.

Still furthermore, the engine was operated by use of gasoline containing 0.3 g of phosphorus (P) per liter of gasoline. The response speed of the oxygen sensor was evaluated after 18 hours of the engine exhaust gas exposure of 400° C. The test result are shown in Table 3.

In order to evaluate the response speed, a voltage of 14 V was applied to the heating resistor, to thereby regulate the temperature of the solid electrolytic member at 700° C.

TABLE 3

| Test Example | Relative density (%) | Porosity (%) | Initial | Response speed After exposure to Pb-containing exhaust gas | After exposure to Si-containing exhaust gas | After exposure to P-containing exhaust gas |
| --- | --- | --- | --- | --- | --- | --- |
| *25 | *28 | *72 | ⊙ | ⊙ | X | ⊙ |
| *26 | *34 | *66 | ⊙ | ⊙ | X | ⊙ |
| 27 | 41 | 59 | ⊙ | ⊙ | ○ | ⊙ |
| 28 | 53 | 47 | ⊙ | ⊙ | ○ | ⊙ |
| 29 | 59 | 41 | ⊙ | ○ | ⊙ | ○ |
| 30 | 61 | 39 | ⊙ | ○ | ⊙ | ○ |
| *31 | *87 | *13 | Δ | X | Δ | X |

In Table 3, the symbol "⊙" refers to the case in which response speed was within 0.75 seconds; the symbol "○" refers to the case in which response speed was within 1.25 seconds; the symbol "Δ" refers to the case in which response speed fell within a range between 1.75 and 2 seconds; and the symbol "X" refers to the case in which response speed exceeds 2 seconds. Values marked with * fall outside of the optimal ranges with respect to the relative density and porosity.

As is apparent from Tables 1 and 2, immediately after firing and after the cooling-heating cycle test, no major exfoliation and cracking are observed in gas sensor elements according to the present invention; i.e., all 300 gas sensor elements of each Test Example, except the elements of Test Examples 8, 9, 17, 18, 22, 23, and 24, although minor cracking is observed in some of the 300 elements of Test Examples 1, 5 and 6 after the cooling-heating cycle test. Therefore, the elements according to the present invention exhibits excellent durability.

As is apparent from Table 3, when a porous member has a relative density of 41–79% and a porosity of 21–59%, the element including the porous member exhibits excellent durability. The results shown in Table 3 show that the elements of Test Examples 25 and 26 exhibit unsatisfactory durability with respect to $SiO_2$ microparticles in gasoline. The results also show that the element of Test Example 31 exhibits unsatisfactory durability with respect to a poisoning substance having a relatively large particle size. The results also show that the element of Test Example 31 exhibits unsatisfactory responsiveness even at an initial stage, since the porosity of the porous member is very low.

Thus, the multi-layer gas sensor elements having structures as described for the present invention exhibit satisfactory responsiveness and excellent durability.

The element of the present invention usually has a length of 37.5 mm. When the element shown in FIG. 1 is employed, a portion of the element—which is about 29.2 mm distant from the back end side of the porous member (the term "back end" refers to the end of the element in a longitudinal direction at which the porous member is not formed—is fixed with a fixing member provided in a metallic shell of a gas sensor. Therefore, the portion is not exposed to a gas to be detected, and the element barely warps during use.

According to the present invention, there can be produced a multi-layer gas sensor element including a porous body, which element does not produce warpage and barely suffers exfoliation and cracking during use; i.e., which element exhibits high durability. According to the present invention, a gas sensor exhibiting high durability can be produced.

While the present invention has been described above with reference to specific embodiments, the present invention is not limited thereto.

This application is based on Japanese Patent Application No. 2000-232400 filed Jul. 31, 2000, the disclosure of which is incorporated herein by reference in its entirety.

What is claimed is:

1. A multi-layer gas sensor element comprising a solid electrolytic member, a substrate, and a porous member, co-fired together, wherein each of the substrate and the porous member has a thickness of at least 1.5 times larger than that of the solid electrolytic member with respect to a lamination direction; the substrate and the porous member face each other and sandwich the solid electrolytic member; a ceramic component constituting the substrate in the highest volume percent thereof is the same as the ceramic component constituting the porous member in the highest volume percent thereof; the solid electrolytic, member also contains said ceramic component which is predominately contained in said substrate in an amount of 20 to 70 mass %; and the volume percent (R2) of the ceramic component contained in the porous member is 80% or more of the volume percent (R1) of the ceramic component contained in the substrate, wherein when the mean grain size of crystals constituting the substrate is referred to as "a1" and the mean grain size of crystals constituting the porous member is referred to as "a2" a value A represented by the following equation (1) falls within a range of from 0.9 to 5 inclusive:

$$A = a1/a2 \qquad (1).$$

2. A multi-layer gas sensor element according to claim 1, wherein the relative density of the porous member is 40–85%.

3. A multi-layer gas sensor element according to claim 1, wherein The porosity of the porous member is 15–60%.

4. A gas sensor comprising a multi-layer gas sensor element as recited in claim 1.

5. A multi-layer gas sensor element according to claim 1, wherein the relative density of the porous member is 40–85%.

6. A multi-layer gas sensor element according to claim 1, wherein the porosity of the porous member is 15–60%.

7. A gas sensor comprising a multi-layer gas sensor element as recited in claim 1.

8. A multi-layer gas sensor element according to claim 1, wherein the relative density of the porous member is 50–70%.

9. A multi-layer gas sensor element according to claim 1, wherein the relative density of the porous member is 50–75%.

10. A multi-layer gas sensor element according to claim 1, wherein the porosity of the porous member is 25–50%.

11. A multi-layer gas sensor element according to claim 1, wherein the porosity of the porous member is 25–50%.

12. A multi-layer gas sensor element according to claim 1, comprising a solid electrolytic member, a substrate, and a porous member, wherein the average thickness of each of the substrate and porous member is at least 1.5 times that of the solid electrolytic member.

13. A multi-layer gas sensor element according to claim 1, wherein the volume percent (R2) of the ceramic component contained in the porous member is 90% or more the volume percent (R1) of the ceramic component contained in the substrate.

14. A multi-layer gas sensor element according to claim 1, wherein the volume percent (R2) of the ceramic component contained in the porous member is 95% or more the volume percent (R1) of the ceramic component contained in the substrate.

15. A multi-layer gas sensor element according to claim 1, wherein the amount of said ceramic component of highest volume percent contained in the substrate is 80 vol % or more.

16. A multi-layer gas sensor element according to claim 1, wherein the volume percent (R2') of crystals formed of said ceramic component of highest volume percent contained in the porous member is 60% or more of the volume percent (R1') or crystals formed of said ceramic component contained in the substrate.

17. A multi-layer gas sensor element according to claim 1, wherein said, ceramic component of highest volume percent is $Al_2O_3$ or $ZrO_2$.

* * * * *